(12) United States Patent
Chang et al.

(10) Patent No.: US 11,939,431 B2
(45) Date of Patent: *Mar. 26, 2024

(54) TEMPERATURE SENSITIVE COMPOSITION FOR TISSUE ADHESION PREVENTION AND APPLICATION THEREOF

(71) Applicant: PROVIEW-MBD BIOTECH CO., LTD., Taipei (TW)

(72) Inventors: Yu-Chia Chang, Taipei (TW); Yunn-Kuen Chang, New Taipei (TW); Wen-Yen Huang, Taipei (TW); Ging-Ho Hsiue, Hsinchu (TW); Hsieh-Chih Tsai, Taipei (TW); Shuian-Yin Lin, Zhubei (TW); Nai-Sheng Hsu, Taoyuan (TW); Tzu-Yu Lin, Taipei (TW)

(73) Assignee: PROVIEW-MBD BIOTECH CO., LTD., Taipei (TW)

( * ) Notice: Subject to any disclaimer, the term of this patent is extended or adjusted under 35 U.S.C. 154(b) by 335 days.

This patent is subject to a terminal disclaimer.

(21) Appl. No.: 17/239,092

(22) Filed: Apr. 23, 2021

(65) Prior Publication Data

US 2021/0330867 A1 Oct. 28, 2021

Related U.S. Application Data

(60) Provisional application No. 63/014,756, filed on Apr. 24, 2020.

(51) Int. Cl.

| *A61L 31/04* | (2006.01) |
| *A61K 31/337* | (2006.01) |
| *A61K 47/34* | (2017.01) |
| *A61L 31/06* | (2006.01) |
| *A61L 31/16* | (2006.01) |
| *C08G 81/00* | (2006.01) |
| *C08L 71/02* | (2006.01) |

(52) U.S. Cl.
CPC ............ *C08G 81/00* (2013.01); *A61K 31/337* (2013.01); *A61K 47/34* (2013.01); *A61L 31/041* (2013.01); *A61L 31/06* (2013.01); *A61L 31/16* (2013.01); *C08L 71/02* (2013.01); *A61L 2300/216* (2013.01); *A61L 2300/416* (2013.01); *A61L 2300/424* (2013.01)

(58) Field of Classification Search
CPC ............... C08G 81/00; C08G 2650/58; C08G 65/3344; C08G 65/33306; A61L 31/041; A61L 31/06; A61L 31/16; A61L 2300/424; A61L 2300/216; A61L 2300/416; C08L 71/02; A61K 31/337; A61K 47/34

See application file for complete search history.

(56) References Cited

U.S. PATENT DOCUMENTS

| 9,327,049 | B2 | 5/2016 | Kim et al. | |
| 9,895,446 | B2 | 2/2018 | Simmons et al. | |
| 10,105,387 | B2 | 10/2018 | Jung et al. | |
| 2009/0196844 | A1 | 8/2009 | Choi et al. | |
| 2015/0335749 | A1 | 11/2015 | Schieker et al. | |
| 2017/0202871 | A1* | 7/2017 | Jung | A61K 47/02 |
| 2019/0375892 | A1 | 12/2019 | Kozlowski et al. | |
| 2021/0332193 | A1* | 10/2021 | Chang | A61L 31/16 |

FOREIGN PATENT DOCUMENTS

WO WO 2010/037044 * 4/2010 ........... A61K 31/765

OTHER PUBLICATIONS

EU Search Report in Application No. 21170082.8 dated Aug. 27, 2021.

* cited by examiner

*Primary Examiner* — Anna R Falkowitz
(74) *Attorney, Agent, or Firm* — Maschoff Brennan

(57) ABSTRACT

The present invention relates to a composition comprising an amino acid-modified polymer, a carboxypolysaccharide, and may further include a metal ion for anti-adhesion and vector application. More specifically, the invention relates to a thermosensitive composition having enhanced mechanical and improved water-erosion resistant properties for efficiently preventing tissue adhesions and can serve as a vector with bio-compatible, bio-degradable/absorbable, and in-vivo sustainable properties.

16 Claims, 4 Drawing Sheets

TEMPERATURE SENSITIVE COMPOSITION FOR TISSUE ADHESION PREVENTION AND APPLICATION THEREOF

CROSS-REFERENCE TO RELATED APPLICATIONS

This application claims the benefit of priority to U.S. Provisional Patent Application No. 63/014,756, filed Apr. 24, 2020, the entirety of which is incorporated by reference herein.

FIELD OF THE INVENTION

The present invention relates generally to tissue adhesion prevention and vector application. Particularly, the invention relates to a thermosensitive composition having enhanced mechanical and improved water-erosion resistant properties for efficiently preventing tissue adhesions and can serve as a vector with bio-compatible, bio-degradable/bioabsorbable, and in-vivo sustainable properties.

BACKGROUND OF THE INVENTION

Tissue or organ adhesions refer to damaged tissues abnormally bind to adjacent tissues or organ surfaces during healing process of the damaged tissues with fibrosis. Thus, tissue adhesions occur when tissue repair mechanisms respond to damages caused by surgery, trauma, and infection, etc. Although tissue adhesion can occur anywhere, the most common factor to cause tissue adhesions is surgery. Tissue adhesions caused by surgical process may result in severe clinical complications such as chronic pain, ischemia, intestinal obstruction, organ dysfunction, and the like, which often require reoperation for adhesiolysis and such a second operation can become life-threatening. The risk of the reoperation for removing postoperative adhesions is high due to introducing of a number of risk factors, such as inadequate anesthesia, excessive bleeding, tissue reaction to foreign materials, and postoperative inflammation, etc. Therefore, in order to prevent the postoperative tissue adhesions, introducing a physical barrier between the damaged tissue and adjacent tissues to obstruct the formation of tissue adhesion has been widely accepted and clinically used.

Polymers or polymeric composites have been widely used as physical tissue barriers for preventing tissue adhesions, and can be generally classified into two types: non-biodegradable and biodegradable/bioabsorbable, based on their biodegradable capability. Biodegradable adhesion barriers have been formulated as many types including films/sheets, liquids, and gels. Although non-biodegradable polymers exhibit excellent adhesion prevention by sustained separating wounds, they have low biocompatibility and thus exist as foreign materials and consequently cause inflammation in wound-surrounding tissues. In the worst scenario, reoperation is required to remove the non-biodegradable polymer when inflammation occurs. Generally, biodegradable polymers present excellent biocompatibility, but their anti-adhesion ability is relative lower than that of non-biodegradable polymers.

Film/sheet-type tissue barrier can physically isolate damaged tissue from the adjacent tissues, hence preventing tissue adhesion. However, it is difficult to handle the film/sheet-type adhesion inhibitor in an emergency surgical condition. Furthermore, film/sheet-type tissue barrier is not suitable to use when the application site is geographically complicated, microscopic, tubular-shaped, or any hard-to-reach area. Another drawback is that the use of film/sheet adhesion inhibitor may result in additional damages to the damage site during the suturing process.

Several liquid adhesion inhibitors have been commercially used, and they are easy to apply as an instillation to wash the entire wound after surgery. However, these products commonly share one shortcoming in insufficient adherence to the application site.

In order to solve these problems, a variety of gel-type adhesion barriers have been developed and applied as polymer solution coating, injectable, spray, and hydrogel coating onto the damaged tissues. These anti-adhesion applications can greatly reduce the operation time compared with the film/sheet-type adhesion inhibitor. However, the gel-type adhesion inhibitor suffers from early absorption due to rapid biodegradation or dissolution by the body, and eventually results in low adhesion preventing efficacy. In addition, most sprayable gel-type adhesion inhibitors use powders to form a cohesive barrier, but their effectiveness in barrier-forming is low. Therefore, it is favorable for a thermo-sensitive adhesion preventer that presents solution properties during operation, but exhibits gel properties after contacting to the damaged tissue. Further, it is highly desirable that such a preventer is also capable of exhibiting strong mechanical strength against rapid in-body dissolution in order to overcome the aforementioned disadvantages of polymer adhesion inhibitors.

Pluronic or Poloxamer, known as a triblock copolymer that generally has a structure of a-poly(ethylene oxide)-b-poly(propylene oxide)-a-poly(ethylene oxide) (PEO-PPO-PEO), is a thermoreversible material that exhibits a thermosensitive sol-gel transition behavior. Generally, pluronic is presence in a solution state at a low temperature, but gelates when temperature increases. Such a sol-gel transition behavior can be influenced by factors including composition, concentration, molecular weight, environmental ion strength, pH value, additives, etc. Therefore, pluronic-based polymers are highly attractive due to their versatile physicochemical and biodegradable properties. Although pluronic exhibits excellent sol-gel phase transition behavior, its hydrous structure is relatively weak and easily dissolved in water. Therefore, pluronic suffers from short of residence time and thus cannot perform time-sufficient adhesion inhibition in the surgical site. In addition, pluronic has been widely studied as a vector in the areas of pharmaceutical science for a long period of time, but it is found to have inadequate mechanical strength and stability which make them inappropriate for vector applications.

Despite current developments in the field, additional improvements are still needed. Ideally, it would be desirable to provide biocompatible, biodegradable/bioabsorbable, and in-vivo sustainable properties to an adhesion inhibitor or a vector with prolonged persistent time, sufficient coverage or delivery as well as with convenient operation for administration. Although such an adhesion barrier or vector has not yet been developed, at least some of these objectives will be achieved by the inventions disclosed hereinafter.

SUMMARY OF THE INVENTION

The first aspect of the present invention is to provide a composition comprising a polymer, and a carboxypolysaccharide, wherein the polymer having any one structure of the following formula (I):

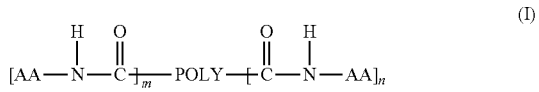

(I)

or a combination thereof,
wherein:
POLY is a triblock copolymer of poly(ethylene oxide) (PEO)-poly(propylene oxide)(PPO)-poly(ethylene oxide) (PEO);
m and n are independently from each other 0 or 1, wherein m and n cannot be 0 simultaneously; and
AA is an amino acid residue, where its amino group directly binds to the chain-end of the POLY to form carbamate (O—C(=O)—NH) linkage.

In one embodiment of the invention, the carboxypolysaccharide is selected from the group consisting of carboxymethylcellulose (CMC), carboxyethylcellulose, hyaluronic acid (HA), alginate, carboxymethyl chitosan, pectin, carboxymethyl dextran, heparin sulfate, and chondroitin sulfate.

In one or more embodiments, the carboxypolysaccharide preferably may be one of carboxymethylcellulose (CMC) and hyaluronic acid (HA).

In one embodiment of the invention, the triblock copolymer of poly(ethylene oxide)(PEO)-poly(propylene oxide) (PPO)-poly(ethylene oxide)(PEO) is selected from Pluronic F-127 (PF127) (also known as Poloxamer 407), Pluronic F-68 (PF68) (also known as Poloxamer 188), and Pluronic L-35 (PL35) (also known as Poloxamer 105).

The second aspect of this invention is to provide a composition comprising a combination of amino acid-modified polymer and a carboxypolysaccharide.

In one embodiment of the invention, the combination of amino acid-modified polymer is consisting of two or more different amino acid-modified polymers.

In one embodiment of the invention, the combination of amino acid-modified polymer is Lysine-modified polymer and Cysteine-modified polymer.

In another embodiment of the invention, the combination of amino acid-modified polymers is Lysine-modified polymer and Serine-modified polymer.

In one embodiment of the invention, the composition furthering comprising a metal ion.

In one embodiment, the metal ion preferably may be a sodium ion.

In one embodiment of the invention, the composition furthering comprising a pharmaceutically active agent.

In one embodiment, the pharmaceutically active agent is selected from the group consisting of anticancer drugs, antibiotics, hemostatic agents, steroids, non-steroidal anti-inflammatory drugs, and hormones. Preferably, the anticancer drug is Paclitaxel.

The third aspect of this invention is to provide a use of the composition for the prevention of post-operative tissue adhesion and drug delivery.

In one or more embodiments, the invention features the composition comprising an amino acid-modified polymer and a carboxypolysaccharide, with improved loading capacity and better release profile for delivery of pharmaceutically active agents.

Obviously, based on the above description of the invention, other various modifications, substitutions, or alterations can be made without departing from the basic technical idea of the invention, with reference to common technical knowledge and conventional means in the art.

BRIEF DESCRIPTION OF THE DRAWINGS

A more complete understanding of the subject matter can be derived by referring to the detailed description and claims when considered in conjunction with the following figures. Each of the following figures is provided for illustration of the performed embodiments only, and the scope of the present invention is not to be restricted by these figures thereto.

DETAILED DESCRIPTION OF THE INVENTION

Technical Problem

Figure 1:
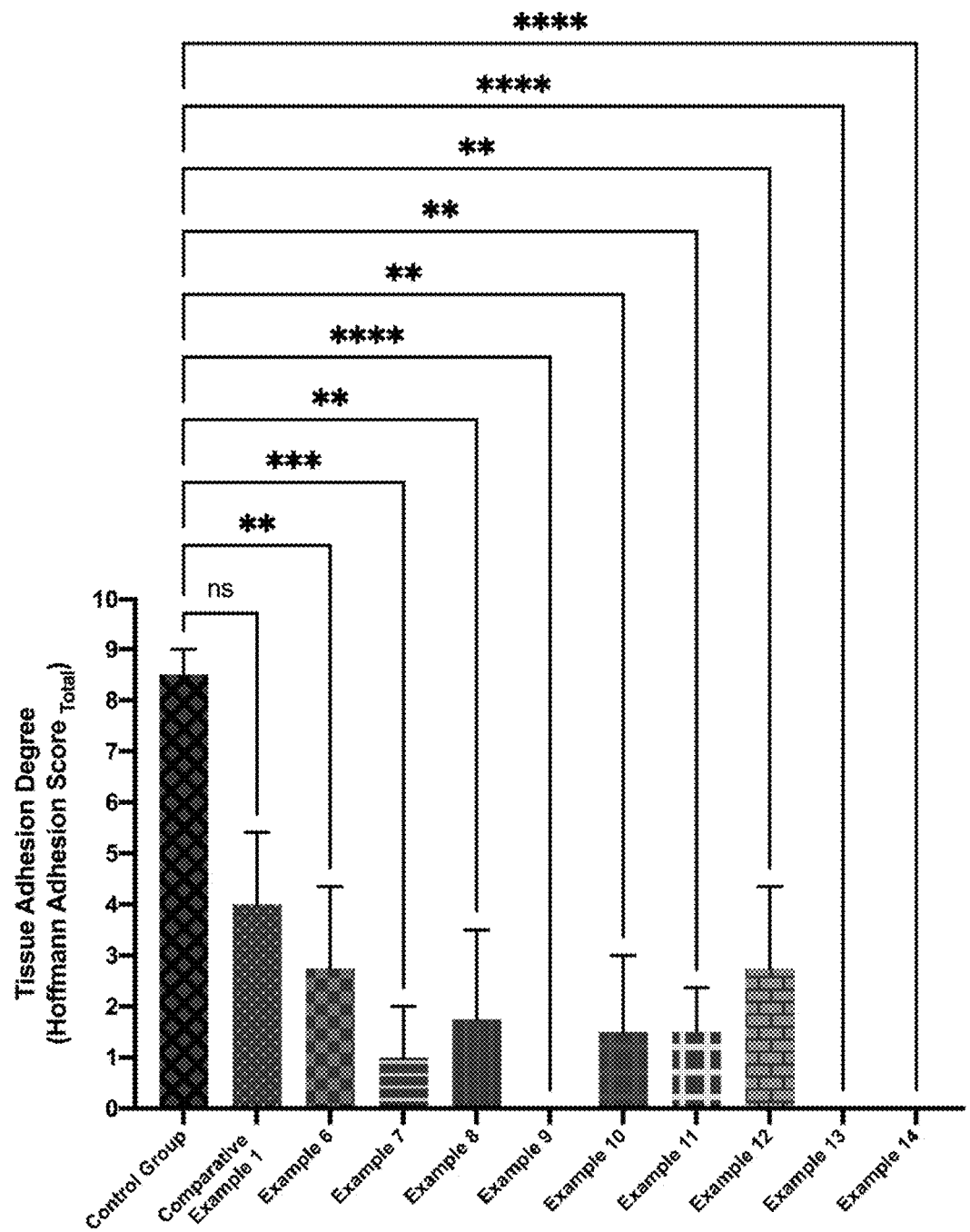
FIG. 1 illustrates the results of evaluating tissue adhesions using the Hoffmann adhesion scoring system. The statistical differences between the control and experimental groups were analyzed by the one-way analysis of variance (ANOVA) with two-tailed calculation using Prism 9 for Mac (GraphPad Software, USA). A value of $p<0.05$ was considered statistical significance, and *indicates $p<0.05$, indicates $p<0.01$, *indicates $p<0.001$, ****indicates $p<0.0001$, and ns represents not statistically significant difference.
Figure 2A:
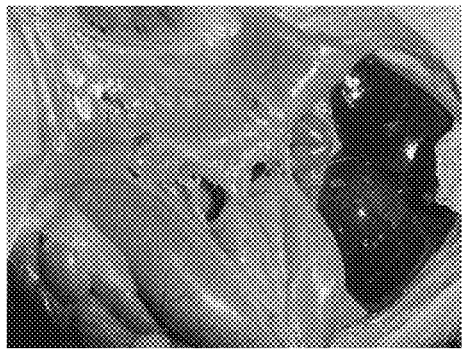
FIG. 2A illustrates the tissue adhesion of the control group.
Figure 2B:
FIG. 2B illustrates the tissue adhesion after treatment of Comparative Example 1.
Figure 2C:
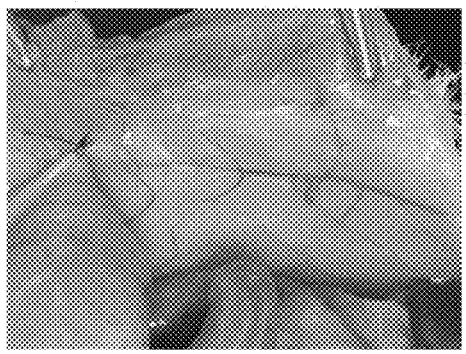
FIG. 2C illustrates the tissue adhesion after treatment of Example 6.
Figure 2D:
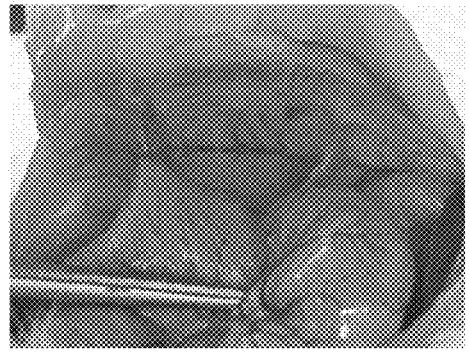
FIG. 2D illustrates the tissue adhesion after treatment of Example 7.
Figure 2E:
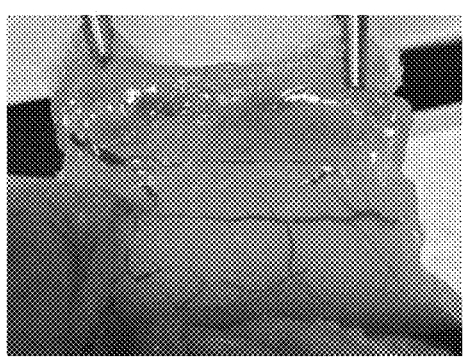
FIG. 2E illustrates the tissue adhesion after treatment of Example 8.
Figure 2F:
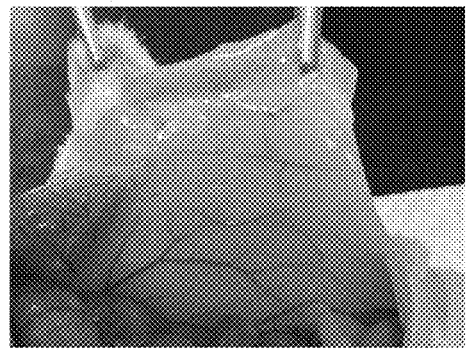
FIG. 2F illustrates the tissue adhesion after treatment of Example 9.
Figure 2G:
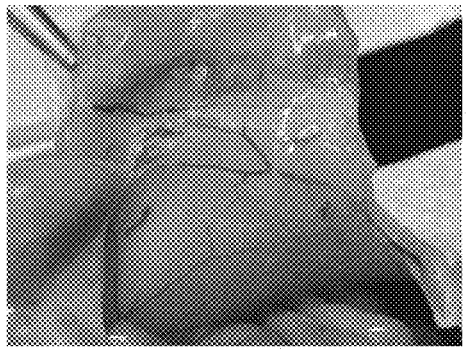
FIG. 2G illustrates the tissue adhesion after treatment of Example 10.
Figure 2H:
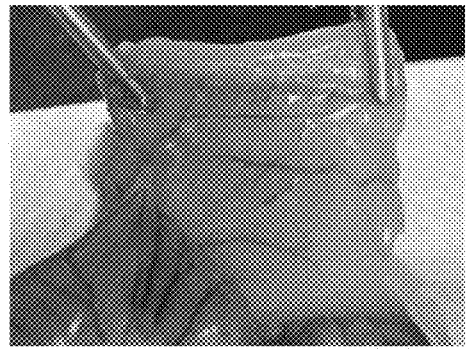
FIG. 2H illustrates the tissue adhesion after treatment of Example 11.
Figure 2I:
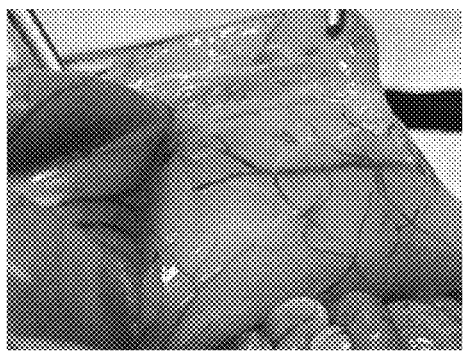
FIG. 2I illustrates the tissue adhesion after treatment of Example 12.
Figure 2J:
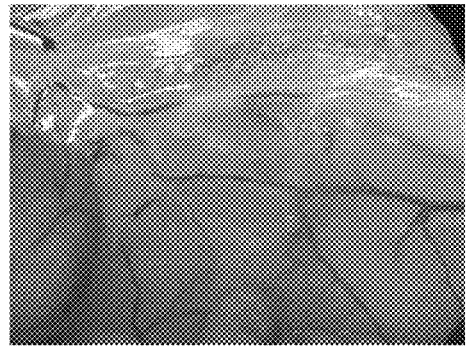
FIG. 2J illustrates the tissue adhesion after treatment of Example 13
Figure 2K:
FIG. 2K illustrates the tissue adhesion after treatment of Example 14

In order to solve the problems of the aforementioned antiadhesive materials, the present invention first provides an amino acid-modified polymer compound which is temperature-sensitive and has a reinforced mechanical strength, an enhanced water-erosion resistance ability, an increased adhesiveness between the polymer and tissues, an enhanced tissue adhesion prevention ability, and an improved release profile in delivery of pharmaceutically active agents as compared with the unmodified polymer counterpart.

Although a kind of the unmodified polymer used in present invention is reported exhibiting an anti-adhesion ability and a thermo-reversible sol-gel phase transition behavior which may be applicable for both adhesion prevention and vector application, it has many defects which cause weak tissue adhesiveness and rapid water-dissolution, leading a low anti-adhesion efficacy in a human body.

In the present invention, however, the provided compound is a polymer chemically modified with amino acids, which not only increase the adhesiveness between the polymer and tissues, but also greatly enhance the mechanical strength of the structure of the polymer. As a result, the amino acid-modified polymers are able to exhibit an increased retention time by up to 16 days or longer, and hence perform better antiadhesion efficacy.

The present invention further provides an advanced composition for an enhanced adhesion inhibitor and a vector, which may comprise an amino acid-modified polymer, a carboxypolysaccharide, and may further include a metal ion.

Although a kind of carboxypolysaccharide used in the present invention has been reported having insufficient persistent time to prevent tissue adhesion and possessing insufficient mechanical strength to serve as a vector due to rapid dissolution by the human body, its excellent tissue adhesiveness, good biocompatibility, biodegradability, high chemical reactivity, and capability of specificity in binding to the target site (tumor), are still beneficial to both adhesion prevention and vector application.

In the present invention, a kind of carboxypolysaccharide which possesses tissue adhesive properties, and may be used to provide additional tissue adhesiveness to the composition. Further, it can also contribute extra interactions toward the polymer and the incorporated amino group at the chain-end of the polymer, leading to an increase of adhesiveness and a reinforcement of mechanical strength for the composition.

In the present invention, a small amount of metal ions may be further used to provide extra binding abilities toward the polymer, the incorporated amino group at the chain-end of the polymer, and the carboxypolysaccharide. Hence, the in-body stability of the polymer composite may be reinforced and stabilized by the addition of metal ion. In addition, the metal ion in the design of the composition may be a body component, and that could act as a non-toxic crosslinking agent to prevent foreign body reaction caused by using a toxic chemical crosslinking agent.

Consequently, the composition comprising an amino acid-modified polymer, and a carboxypolysaccharide together with a metal ion, is capable of providing sufficient sustainability, effective antiadhesion ability, convenient of operation, sustainable drug delivery without possessing dangerous adverse effects, which is compliant with the objectives disclosed in the present invention.

Technical Solution

The present invention first provides a temperature-sensitive compound that is consisting of an amino acid-modified polymer, which may be solely used as an adhesion inhibitor, a drug vector, or a main component for those applications.

The present invention further provides a composition for an advanced tissue adhesion inhibitor and a vector, which may comprise an amino acid-modified polymer and a carboxypolysaccharide; wherein, the amino acid-modified polymer may be a polymer combination, which is consisting of two or more different amino acid-modified polymers.

The present invention further provides a composition for an enhanced tissue adhesion inhibitor and a vector, which may comprise an amino acid-modified polymer, a carboxypolysaccharide, and may further include a metal ion.

Before detailed describing one or more embodiments of the present invention, it is important to be noted that, as used in this specification and the claims, the singular forms "a.", "an." and "the" include plural referents unless the context clearly specified otherwise. Therefore, for example, reference to "an amino acid" includes a single amino acid as well as two or more of the same or different amino acids, reference to "chain-end of polymer" includes a single chain-end as well as two of the same or different chain-end of polymers, and the like.

In describing and claiming the present invention, unless otherwise specified, the terms used herein have the following definitions:

As used herein, the terms "comprises," "comprising," "includes," "including," "has," "having" or any other variation thereof are intended to cover a non-exclusive inclusion. For example, a component, structure, article, or apparatus that comprises a list of elements is not necessarily limited to only those elements but may include other elements not expressly listed or inherent to such component, structure, article, or apparatus.

The term "Amino acids" refers to the structural units of proteins. The twenty amino acids encoded by the genetic code are called "standard amino acids." These amino acids have the structure $H_2N$—CHR—COOH, where R is a side chain specific to the amino acids. Standard amino acids are Alanine, Arginine, Aspargine, Aspartic acid, Cysteine, Glutamic acid, Glutamine, Glycine, Histidine, Isoleucine, Leucine, Lysine, Methionine, Phenylalanine, Proline, Serine, Threonine, Tryptophan, Tyrosine, and Valine. Amino acids can be classified into five groups, specifically, hydrophobic amino acids, hydrophilic amino acids, basic amino acids, acidic amino acids, and aromatic amino acids. As used herein, amino acids can be present in two stereoisometric forms, called "D." and "L." described herein.

The amino acid-modified polymer and composition of the present invention can be administered to prevent adhesions in the context of any of a variety of postoperative types. As used herein, the term "postoperative" refers to examples of postoperative procedures in which the amino acid-modified polymer and composition of the invention are of use include, without limitation, abdominal, abdominopelvic, ophthalmic, orthopedic, gastrointestinal, thoracic, cranial, head and neck, cardiovascular, gynecological, obstetric, joint (e.g., arthroscopic), urologic, plastic, reconstructive, musculoskeletal, and neuromuscular surgeries.

According to the present invention, it is possible to effectively prevent postoperative tissues adhesion. The antiadhesive polymer and composition thereof used in the present invention may have any form such as powder, solution or gel form, and therefore, for example, is easy to perform even in relatively localized surgery such as endoscopic surgery.

The antiadhesive polymer and composition thereof used in the present invention can be applied on the surgery by, for example, coating or spraying onto a wound site and the surfaces of organs located around the wound site or surrounding tissues. The application may be performed at one time or with a plurality of times coating or spraying onto a local portion of the surface of the target organ or surrounding tissues. Also, a coating or spraying device may be used. The device can be a prefilled syringe. The dose can be appropriately selected or adjusted by a person skilled in the art.

The term "amino acid-modified polymer" refers to a polymer with its chain-end bound with an amino acid and/or a polyamino acid through a carbamate linkage, wherein the polymer may be a polyethylene oxide-containing copolymer, and the polyethylene oxide is a hydrophilic polymer consisting of a repeated unit of compound including —(O—CH$_2$—CH$_2$)—. The copolymer may include another compound which is copolymerized with the polyethylene oxide. Another compound may be two or more, for example, two or three or more selected from the group consisting of polypropylene oxide (PPO), polyethylene glycol (PEG), poly-L-lysine (PLL), poly(dioxanone) (PDO), polyglycolic acid (PGA), polylactic acid (PLA), poly(DL-lactide-co-glycolide) (PLGA), polycaprolactone (PCL).

Further, the copolymer may be a Pluronic that is a triblock polymer, consisting of poly(ethylene oxide)(PEO)-poly(propylene oxide)(PPO)-poly(ethylene oxide)(PEO). The structure of the amino acid-modified polymer is represented by the following Formula (I):

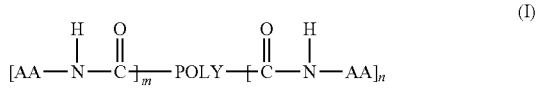

(I)

wherein:

POLY represents a copolymer comprising poly(ethylene oxide)(PEO)-poly(propylene oxide)(PPO)-poly(ethylene oxide)(PEO), m and n are independently from each other 0 or 1, wherein m and n cannot be 0 simultaneously, and AA represents an amino acid or a polyamino acid residue, where its amino group directly binds to a chain-end of the POLY to form a carbamate bond, wherein AA is selected from the groups consisting of hydrophobic amino acids, basic amino acids, acidic amino acid, aromatic amino acids, and hydrophilic amino acids. Wherein, the hydrophobic amino acids comprising hydrophobic amino acids and/or hydrophobic polyamino acids, for example, Glycine, Alanine, Valine, Methionine, Leucine, Isoleucine, Phenylalanine and polymers thereof; the basic amino acids comprising basic amino acids and/or basic polyamino acids, for example, Lysine, Histidine, Arginine and polymers thereof; the acidic amino acids comprising acidic amino acids and/or acidic polyamino acids, for example, Aspartic acid, Asparagine, glutamic acid and polymers thereof; the aromatic amino acids comprising aromatic amino acids and/or aromatic polyamino acids, for example, Tyrosine, Tryptophan and polymers thereof; and the hydrophilic amino acids comprising hydrophilic amino acids and/or hydrophilic polyamino acids, for example, Serine, Threonine, Cysteine, Proline and polymers thereof.

The term "amino acid-modified polymer composition" refers to a composition comprising any one of polymer having a structure of Formula (I), or combinations thereof.

The copolymer, POLY, has an average molecular weight ranging from 1,000 to 20,000 Daltons depending on the properties. Further, the copolymer, POLY, is selected from the group consisting of Pluronic F-127 (PF127) (also known as Poloxamer 407), Pluronic F-68 (PF68) (also known as Poloxamer 188), and Pluronic L-35 (PL35) (also known as Poloxamer 105).

The term "in an amount of" refers to the weight of any one of the polymer or combinations thereof based on the final composition in the present invention. The polymer or combinations thereof may be in an amount of 5% to 30% by weight, 7% to 25% by weight, preferably 10% to 20% by weight, 12% to 18% by weight, and more preferably 13% to17% by weight of the final composition.

The term "polymer combination" refers to a combination that is mixed two or more of the different amino acid-modified polymers thereof. For the combination of the two amino acid-modified polymers, the content of the polymers may be selected from a particular weight ratio, ranging from 1% : 99% by weight, 10% : 90% by weight, 20% : 80% by weight, 30% : 70% by weight, 40% : 60% by weight, and 50% : 50% by weight of the final composition. For the combination of more than two amino acid-modified polymers, the content of all the polymer components in a combination is 100% by weight of the final combination, and the content of the polymer components may be selected from any ratio, for example, the content of any polymer component in the combination may be used in an amount of more than 0% by weight, and less than 100% by weight of the final combination.

The amino acid-modified polymer composition may comprise a carboxypolysaccharide. The carboxypolysaccharide may provide an additional interaction to enhance the mechanical strength of the composition and thus increases the retention time of the composition. Further, the carboxypolysaccharide may offer the composition an improved mucoadhesive property, which may increase the wound covering time of the composition.

The carboxypolysaccharide may be one or more selected from the group including carboxymethylcellulose (CMC), carboxyethylcellulose, hyaluronic acid (HA), alginate, carboxymethyl chitosan, pectin, carboxymethyl dextran, and glycosaminoglycans such as heparin, heparin sulfate, and chondroitin sulfate The carboxypolysaccharide may be selected from materials having a molecular weight in a range of 50 kg/mol to 4,000 kg/mol, depending on properties. The molecular weight of the carboxypolysaccharide may be 50 kg/mol to 4,000 kg/mol, 100 kg/mol to 3,500 kg/mol, 500 kg/mol to 3,000 kg/mol, or 1,000 kg/mol to 2,500 kg/mol.

The content of the carboxypolysaccharide may be selected from a range of 0.1% to 20% by weight, 0.5% to 15% by weight, preferably 1% to 10% by weight, 2% to 8% by weight and more preferably 3% to 7% by weight of the final composition.

The amino acid-modified polymer composition may further comprise a metal ion. The metal ion may provide an ionic bond between the amino acid groups terminated at the chain-end of the copolymer, a hydrogen bond between the copolymer and the carboxypolysaccharide, a hydrogen bond between amino acid groups terminated the copolymer, a hydrogen bond between the amino group terminated at the chain-end of the copolymer and the carboxypolysaccharide. Therefore, the composition may form a stable hydrogel due to the hydrogen and ionic bonds induced enhancement. Additionally, the addition of a metal may be used to adjust the sol-gel transition temperature of the composition.

The metal ion may be one of more selected from the group consisting of Li$^+$, Na$^+$, K$^+$, Ag$^+$, Cu$^{+2}$, Zn$^{+2}$, Sn$^{+2}$, Fe$^{+3}$, Al$^{+3}$, Fe$^{+3}$, Co$^{+3}$, Ni$^{+3}$, Ce$^{+4}$, Se$^{+4}$, and Ti$^{+4}$.

The content of the metal ion may be approximately selected from a range of 0.5% to 2% by weight of the final composition.

The term "biocompatible" refers to a material that is substantially non-toxic, non-immunogenic and non-irritant to a recipient's cells in the quantities and at the location used, and also does not elicit or cause a significant deleterious or undesirable effect on the recipient's body at the location used.

The term "adhesion prevention" refers to administering a composition for prevention of adjacent tissues or organ surfaces from adhering together so as to cause a reduction in the number of adhesions, extent of adhesions (e.g., area), and/or severity of adhesions (e.g., thickness or resistance to mechanical or chemical disruption) relative to the number, extent, and/or severity of adhesions that would occur without such administration.

The term "adhesion inhibitor" refers to administering or applying a composition for inhibiting adjacent tissues or surface of organs adhering together.

The term "vector" refers to a carrier that is capable of carrying and releasing pharmaceutically active agents.

The term "vector applications" refers to applications which require a carrier to deliver and release pharmaceutically active agents.

The term "carbamate linkage" refers to a carbamate binding between an amino group of an amino acid and a carbonate ester at the chain-end of a polymer. The chemical structure of such carbamate linkage is represented as the following Formula (II):

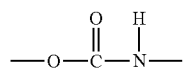
(II)

The term "pharmaceutically active agent" refers to any medicinal useful substance which may have certain therapeutic, preventive and/or diagnostic effects to a human or animal body. Herein, the pharmaceutically active agent is selected from the group consisting of anticancer drugs, antibiotics, hemostatic agents, steroids, non-steroidal anti-inflammatory drugs, hormones, analgesics, and anesthetics. Preferably, the anticancer drugs is Paclitaxel.

The term "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient.

In this invention, a composition comprising the amino acid-modified polymer and polysaccharide may presence as a hydrogel, and may be temperature-sensitive. Therefore, the composition may allow a reversible transitioning between sol and gel states upon change of temperature, and the temperature of the sol-gel phase transition (gelation) may be controlled by adjusting the contents of the polymer. The polymer composition may present a sol state at room temperature, but transform into a gel state when temperature is below human body temperature, herein between 28° C. to 36° C., and thus they may be injected or sprayed into a surgical site in a human or animal body, providing sufficient wound coverage. After being applied into the surgical site, the polymer composition may subsequently undergo a gelation and adhere to the wound as a barrier to prevent tissue adhesion.

The polymer composition may allow a thermosensitive sol-gel state transitioning which enables them to act as a vector to perform transdermal, injectable, sprayable and controlled delivery of many pharmaceutically active agents.

Pluronic, a copolymer comprising poly(ethylene oxide) (PEO)-poly(propylene oxide)(PPO)-poly(ethylepne oxide) (PEO), has been reported exhibiting a thermo-reversible sol-gel phase transition behavior and a certain anti-adhesion ability, which is widely studied for both vector application and adhesion prevention. However, it has a low anti-adhesion efficiency and poor drug release profile in a human body caused by poor mechanical strength, weak tissue adhesiveness, and rapid water dissolution (less than 2 days).

In this invention, pure Pluronic, which serves an unmodified comparative example of our compounds, is used as a comparison to evaluate the inventive steps of the present invention on the adhesion prevention ability and drug releasee efficacy contributed from the present composition comprising an amino acid-modified Pluronic and a carboxypolysaccharide, with or without a metal ion. Accordingly, as a result of extensive research, the inventors of this application have found that the composition may: (1) enhance the mechanical strength of the polymer structure, (2) increase the water-erosion resistance ability, (3) increase the adhesiveness between the polymer and tissues, (4) enhance the tissue adhesion prevention ability, and (5) improve the release profile in delivery of pharmaceutically active agents.

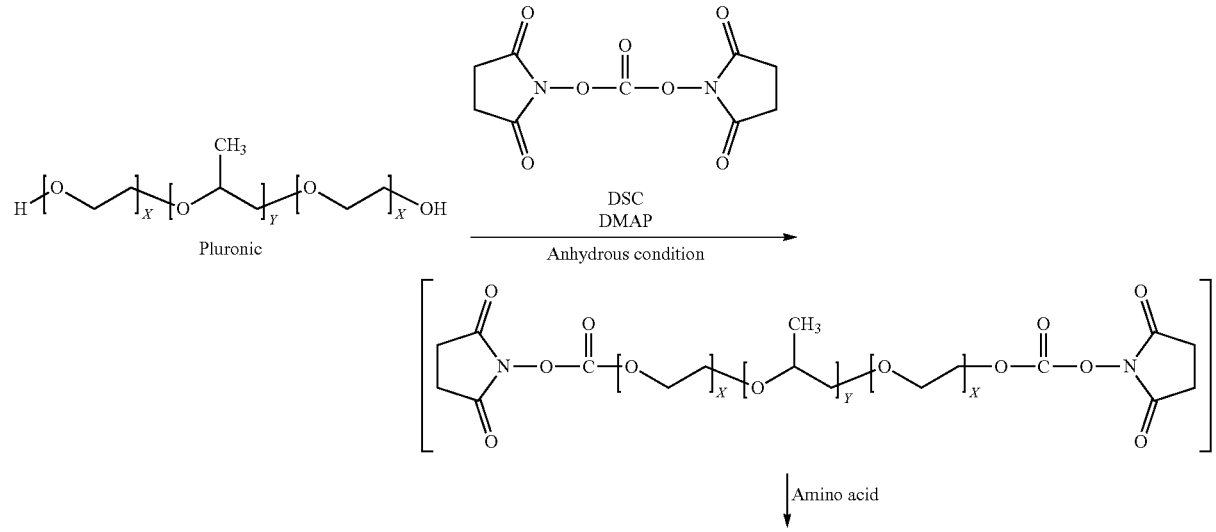

REACTION SCHEME

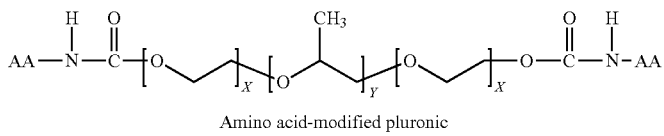

Amino acid-modified pluronic

Experimental

The present invention is performed using conventional technique of organic synthesis, biochemistry, rheology, and the like, which are known to those skilled in the art.

Hereinafter, the present invention will be described in more detail with reference to examples. However, each of the following examples is provided for illustration of the performed embodiments only, and the scope of the present invention is not to be restricted by these examples thereto.

Materials

The chemicals used to perform the Examples and Comparative Examples are as follows:

Pluronic-F127 (12,500 Da), Pluronic F-68 (8,400 Da), and Pluronic L-35 (1,900 Da) were available from BASF Corporation. Anhydrous tetrahydrofuran (hereinafter referred to as "THF"), 4-dimethylaminopyridine (hereinafter referred to as "DMAP"), and anhydrous dimethyl sulfoxide (hereinafter referred to as "anhydrous DMSO") were available from Acrose. N, N'-disuccinimidyl carbonate (hereinafter referred to as "DSC") and Paclitaxel (hereinafter referred to as "PTX") were available from Fluorochem. L-Aspartic acid, L-Asparagine, L-Lysine, L-Serine, and L-Tyrosine were available from Acrose. L- Leucine, L-Cysteine, and L-Methionine were available from cj haide (ningbo) biotech co. ltd. Carboxymethylcellulose (CMC) was available from Sigma, hyaluronic acid (HA) was available from Kewpie, and NaCl was available from Acrose.

EXAMPLE 1

Preparation of Hydrophobic Amino Acid-Modified Pluronic (1) Leucine-Modified Pluronic F-127

A hydrophobic amino acid, L-Leucine, in an amount of 4.8 mmole was dissolved in an alkaline solution to form an amino acid solution. Pluronic F-127 in an amount of 0.6 mmole and 4.8 mmole of DMAP were dissolved in 30 mL of anhydrous THF to obtain a clear solution. After 30 minutes stirring, 10 mL of anhydrous DMSO containing 4.8 mmole of DSC were dropwise added within 1 hour, and the mixture was stirred at room temperature for 24 hours. Process was all carried out under nitrogen atmosphere. After 24 hours, the Leucine-contained solution was added and the mixture was kept stirring for 24 hours. The resulting Leucine-modified Pluronic solution was purified by dialysis, and was dried by lyophilization to yield white polymer powders (yield: 45%). $^1$H NMR (D$_2$O): δ 4.30, 4.21 (m, —CH$_2$—O—(C=O)—NH—), 4.01 (m, —O—(C=O)—NH—CH—), 1.70 (m, —CH$_2$—CH—(CH$_3$)$_2$), 1.60 (m, —CH—(CH$_3$)$_2$), 0.96 (m, —CH—(CH$_3$)$_2$); FTIR: 780 cm$^{-1}$ (—NH wag), 1531 cm$^{-1}$ (—CNH), 1569 cm$^{-1}$ (—(C=O)—NH—), 1731 cm$^{-1}$ (—(C=O)).

The exemplary chemical structure of the Leucine-modified Pluronic F-127 is provided as following:

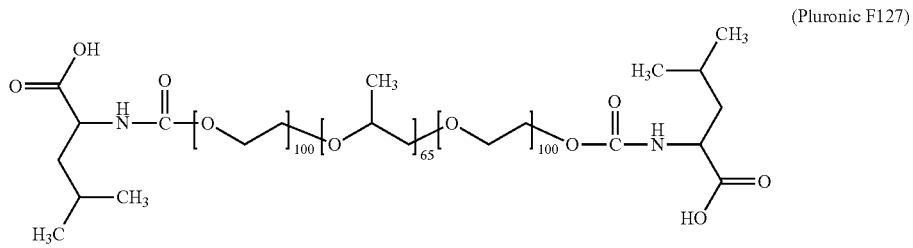

(Pluronic F127)

(2) Leucine-Modified Pluronic F-68

A hydrophobic amino acid, L-Leucine, in an amount of 4.8 mmole was dissolved in an alkaline solution to form an amino acid solution. Pluronic F-68 in an amount of 0.6 mmole and 4.8 mmole of DMAP were dissolved in 30 mL of anhydrous THF to obtain a clear solution. After 30 minutes stirring, 10 mL of anhydrous DMSO containing 4.8 mmole of DSC were dropwise added within 1 hour, and the mixture was stirred at room temperature for 24 hours. Process was all carried out under nitrogen atmosphere. After 24 hours, the Leucine-contained solution was added and the mixture was kept stirring for 24 hours. The resulting Leucine-modified Pluronic solution was purified by dialysis, and was dried by lyophilization to yield white polymer powders (yield: 40%). $^1$H NMR (D$_2$O): δ 4.28, 4.23 (m, —CH$_2$—O—(C=O)—NH—), 4.06 (m, —O—(C=O)—NH—CH—), 1.72 (m, —CH$_2$—CH—(CH$_3$)$_2$), 1.62 (m, —CH—(CH$_3$)$_2$), 0.97 (m, —CH—(CH$_3$)$_2$); FTIR: 780 cm$^{-1}$ (—NH wag), 1531 cm$^{-1}$ (—CNH), 1569 cm$^{-1}$ (—(C=O)—NH—), 1731 cm$^{-1}$ (—(C=O)).

The exemplary chemical structure of the Leucine-modified Pluronic F-68 is provided as following:

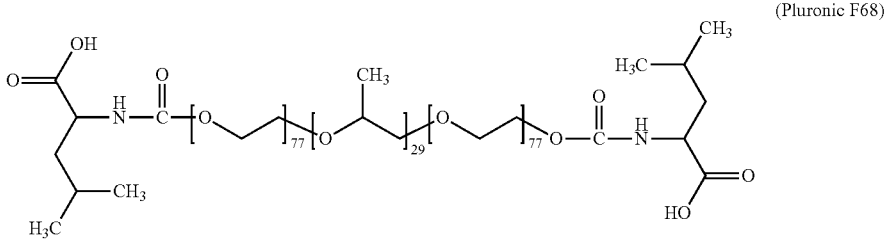

(Pluronic F68)

(3) Leucine-Modified Pluronic L-35

A hydrophobic amino acid, L-Leucine, in an amount of 4.8 mmole was dissolved in an alkaline solution to form an amino acid solution. Pluronic L-35 in an amount of 0.6 mmole and 4.8 mmole of DMAP were dissolved in 30 mL of anhydrous THF to obtain a clear solution. After 30 minutes stirring, 10 mL of anhydrous DMSO containing 4.8 mmole of DSC were dropwise added within 1 hour, and the mixture was stirred at room temperature for 24 hours. Process was all carried out under nitrogen atmosphere. After 24 hours, the Leucine-contained solution was added and the mixture was kept stirring for 24 hours. The resulting Leucine-modified Pluronic solution was purified by dialysis, and was dried by lyophilization to yield white polymer powders (yield: 35%). $^1$H NMR (D$_2$O): δ 4.30 (m, —O—(C=O)—NH—CH—), 4.22 (m, —CH$_2$—O—(C=O)—NH—), 1.70 (m, —CH$_2$—CH—(CH$_3$)$_2$), 1.61 (m, —CH—(CH$_3$)$_2$), 0.97 (m, —CH—(CH$_3$)$_2$); FTIR: 780 cm$^{-1}$ (—NH wag), 1531 cm$^{-1}$ (—CNH), 1569 cm$^{-1}$ (—(C=O)—NH—),1731 cm$^{-1}$ (—(C=O)).

The exemplary chemical structure of the Leucine-modified Pluronic L-35 is provided as following:

(Pluronic L35)

(4) Methionine-Modified Pluronic F-127

A hydrophobic amino acid, L-Methionine, in an amount of 4.8 mmole was dissolved in an alkaline solution to form an amino acid solution. Pluronic F-127 in an amount of 0.6 mmole and 4.8 mmole of DMAP were dissolved in 30 mL of anhydrous THF to obtain a clear solution. After 30 minutes stirring, 10 mL of anhydrous DMSO containing 4.8 mmole of DSC were dropwise added within 1 hour, with continued stirring at room temperature for 24 hours. Process was all carried out under nitrogen atmosphere. After 24 hours, the solution containing Methionine was added and the mixture was stirred for 24 hours. The resulting Methionine-modified Pluronic solution was purified by dialysis, and was dried by lyophilization to yield white polymer powders (yield: 45%). $^1$H NMR (D$_2$O): δ 4.30 (m, —O—(C=O)—NH—CH—), 4.23 (m, —CH$_2$—O—(C=O)—NH—), 2.61 (m, —CH$_2$—CH$_2$—S—CH$_3$), 2.16 (s, —S—CH$_3$), 2.13, 1.96 (m, —CH$_2$—CH$_2$—S—CH$_3$); FTIR: 1215 cm$^{-1}$ (—CNH), 1603 cm$^{-1}$ (—(C=O)—NH—), 1733 cm$^{-1}$ (—(C=O)).

EXAMPLE 2

Preparation of Basic Amino Acid-Modified Pluronic

Lysine-Modified Pluronic F-127

A basic amino acid, L-Lysine, in an amount of 2.4 mmole was dissolved in distilled water to form an amino acid solution. Pluronic F-127 in an amount of 0.6 mmole and 4.8 mmole of DMAP were dissolved in 30 mL of anhydrous THF to obtain a clear solution. After 30 minutes stirring, 10 mL of anhydrous DMSO containing 4.8 mmole of DSC were dropwise added within 1 hour, the mixture was stirred at room temperature for 24 hours. Process was all carried out under nitrogen atmosphere. After 24 hours, the Lysine-contained solution was added and the mixture was kept stirring for 24 hours. The resulting Lysine-modified Pluronic solution was purified by dialysis, and was dried by lyophilization to yield white polymer powders (yield: 45%). $^1$H NMR (D$_2$O): δ 4.25 (m, —CH$_2$—O—(C=O)—NH—), 3.16 (m, —O—(C=O)—NH—CH$_2$—), 1.81, 1.70 (m, NH—CH$_2$—CH$_2$—CH$_2$—CH$_2$), 1.57 (m, NH—CH$_2$—CH$_2$—CH$_2$—CH$_2$—), 1.41 (m, NH—CH$_2$—CH$_2$—CH$_2$—

$CH_2$—, 2H); FTIR: 776 cm$^{-1}$ (—NH wag), 1557 cm$^{-1}$ (—CNH), 1710 cm$^{-1}$ (—(C═O)).

EXAMPLE 3

Preparation of Acidic Amino Acid-Modified Pluronic (1) Aspartic Acid-Modified Pluronic F-127

An acidic amino acid, L-Aspartic acid, in an amount of 4.8 mmole was dissolved in an alkaline solution to form an amino acid solution. Pluronic F-127 in an amount of 0.6 mmole and 4.8 mmole of DMAP were dissolved in 30 mL of anhydrous THF to obtain a clear solution. After 30 minutes stirring, 10 mL of anhydrous DMSO containing 4.8 mmole of DSC were dropwise added within 1 hour, and the mixture was with continued stirring at room temperature for 24 hours. Process was all carried out under nitrogen atmosphere. After 24 hours, the solution containing Aspartic acid was added and the mixture was stirred for 24 hours. The resulting Aspartic acid-modified Pluronic solution was purified by dialysis, and was dried by lyophilization to yield white polymer powders (yield: 45%). $^1$H NMR (D$_2$O): δ 4.38 (m, —O—(C═O)—NH—C$\underline{H}$—), 4.26 (m, —C$\underline{H_2}$—O—(C═O)—NH—), 2.70, 2.51 (m, —C$\underline{H_2}$—(C═O)—OH); FTIR: 776 cm$^{-1}$ (—NH wag), 1557 cm$^{-1}$ (—CNH), 1710 cm$^{-1}$ (—(C═O)).

(2) Asparagine-Modified Pluronic F-127

An acidic amino acid, L-Asparagine, in an amount of 2.4 mmole was dissolved in an alkaline solution to form an amino acid solution. Pluronic F-127 in an amount of 0.6 mmole and 4.8 mmole of DMAP were dissolved in 30 mL of anhydrous THF to obtain a clear solution. After 30 minutes stirring, 10 mL of anhydrous DMSO containing 4.8 mmole of DSC were dropwise added within 1 hour, and the mixture was kept stirring at room temperature for 24 hours. Process was all carried out under nitrogen atmosphere. After 24 hours, the solution containing Asparagine was added and the mixture was stirred for 24 hours. The resulting Aspartic acid-modified Pluronic solution was purified by dialysis, and was dried by lyophilization to yield white polymer powders (yield: 45%). $^1$H NMR (D$_2$O): δ 4.35 (m, —O—(C═O)—NH—C$\underline{H}$—), 4.27 (m, —C$\underline{H_2}$—O—(C═O)—NH—), 2.82, 2.68 (m, —C$\underline{H_2}$—(C═O)—NH$_2$); FTIR: 1416 cm$^{-1}$ (—CN), 1680 cm$^{-1}$ (—(C═O—NH—), 1720 cm$^{-1}$ (—(C═O)).

EXAMPLE 4

Preparation of Aromatic Amino Acid-Modified Pluronic Tyrosine-Modified Pluronic F-127

An aromatic amino acid, L-Tyrosine, in an amount of 4.8 mmole was dissolved in an alkaline solution to form an amino acid solution. Pluronic F-127 in an amount of 0.6 mmole and 4.8 mmole of DMAP were dissolved in 30 mL of anhydrous THF to obtain a clear solution. After 30 minutes stirring, 10 mL of anhydrous DMSO containing 4.8 mmole of DSC were dropwise added within 1 hour, and the mixture was kept stirring at room temperature for 24 hours. Process was all carried out under nitrogen atmosphere. After 24 hours, the solution with Tyrosine was added and the mixture was stirred for 24 hours. The resulting Tyrosine-modified Pluronic solution was purified by dialysis, and was dried by lyophilization to yield white polymer powders (yield: 40%). $^1$H NMR (D$_2$O): δ 7.20 (d, $^2$C$\underline{H}$, $^6$C$\underline{H}$-phenyl ring), 6.89 (d, $^3$C$\underline{H}$, $^5$C$\underline{H}$-phenyl ring), 4.21 (m, —C$\underline{H_2}$—O—(C═O)—NH—), 4.11 (m, —O—(C═O)—NH—C$\underline{H}$—), 3.15, 2.83 (m, —C$\underline{H_2}$-ph); FTIR: 1403 cm$^{-1}$ (—CN), 1517 cm$^{-1}$ (—CNH), 1604 cm$^{-1}$ (—C—C—/C═C), 1710 cm$^{-1}$ (—(C═O)).

EXAMPLE 5

Preparation of Hydrophilic Amino Acid-Modified Pluronic (1) Serine-Modified Pluronic F-127

A hydrophilic amino acid, L-Serine, in an amount of 4.8 mmole was dissolved in distilled water to form an amino acid solution. Pluronic F-127 in an amount of 0.6 mmole and 4.8 mmole of DMAP were dissolved in 30 mL of anhydrous THF to obtain a clear solution. After 30 minutes stirring, 10 mL of anhydrous DMSO containing 4.8 mmole of DSC were dropwise added within 1 hour, and the mixture was continuous stirred at room temperature for 24 hours. Process was all carried out under nitrogen atmosphere. After 24 hours, the solution with Serine was added and the mixture was stirred for 24 hours. The resulting Serine-modified Pluronic solution was purified by dialysis, and was dried by lyophilization to yield white polymer powders (yield: 40%). $^1$H NMR (D$_2$O): δ 4.30 (m, —C$\underline{H_2}$—O—(C═O)—NH—), 4.16 (m, —O—(C═O)—NH—C$\underline{H}$—), 3.93, 3.83 (m, —C$\underline{H_2}$—OH); FTIR: 1410 cm$^{-1}$ (—CN), 1604 cm$^{-1}$ (—(C═O)—NH—), 1720 cm$^{-1}$ (—(C═O)).

(2) Cysteine-Modified Pluronic F-127

A hydrophilic amino acid, L-Cysteine, in an amount of 4.8 mmole was dissolved in an alkaline solution to form an amino acid solution. Pluronic F-127 in an amount of 0.6 mmole and 4.8 mmole of DMAP were dissolved in 30 mL of anhydrous THF to obtain a clear solution. After 30 minutes stirring, 10 mL of anhydrous DMSO containing 4.8 mmole of DSC were dropwise added within 1 hour, and the mixture was with continued stirring at room temperature for 24 hours. Process was all carried out under nitrogen atmosphere. After 24 hours, the solution containing Cysteine was added and the mixture was kept stirring for 24 hours. The resulting Cysteine-modified Pluronic solution was purified by dialysis, and was dried by lyophilization to yield white polymer powders (yield: 50%). $^1$H NMR (D$_2$O): δ 4.46 (m, —O—(C═O)—NH—C$\underline{H}$—), 4.27 (m, —C$\underline{H_2}$—O—(C═O)—NH—), 3.20, 2.98 (m, —C$\underline{H_2}$—SH); FTIR: 1412 cm$^{-1}$ (—CN), 1515 cm$^{-1}$ (—CNH), 1604 cm$^{-1}$ (—(C═O)—NH—), 1700 cm$^{-1}$ (—(C═O)).

EXAMPLE 6-9

Preparation of Thermosensitive Composition for Antiadhesion

The temperature-sensitive compositions were prepared using different components and predetermined ratios of contents, and the formulations are shown in the following Table 1. Briefly, a quantity of sodium chloride (NaCl) was firstly dissolved in distilled water to obtain a stock solution with a concentration of 20% (w/v). Then, an amount of polymer powders prepared from Example 2 was mixed with a quantity of hyaluronic acid (HA) or carboxymethylcellulose (CMC), an amount of distilled water, and with or without solution of sodium chloride (NaCl) to obtain a thermosensitive composition containing Lysine-modified Pluronic F-127, hyaluronic acid or carboxymethylcellulose, and sodium chloride or without sodium chloride.

TABLE 1

| | Content (w/v %) | | | |
|---|---|---|---|---|
| Component | Example 6 | Example 7 | Example 8 | Example 9 |
| Lysine-Pluronic F-127 | 15 | 15 | 15 | 15 |
| Hyaluronic acid | 0.5 | 0.5 | 0 | 0 |
| Carboxymethylcellulose | 0 | 0 | 5 | 5 |
| NaCl | 0 | 1 | 0 | 0.1 |

EXAMPLE 10-14

Preparation of Thermosensitive Composition for Antiadhesion and Drug Delivery

The temperature-sensitive compositions were prepared using the same manner as in Examples 6-9, except that each of the main polymer component has been replaced with a combination of Lysine- and Cysteine-modified Pluronic F-127, where the content of Lysine is 80% by weight, and Cysteine is 20% by weight of the final combination. The formulations of the prepared compositions are shown in the following Table 2.

TABLE 2

| | Content (w/v %) | | | | |
|---|---|---|---|---|---|
| Component | Example 10 | Example 11 | Example 12 | Example 13 | Example 14 |
| Lysine-and Cysteine-Pluronic F-127 (Lysine/Cysteine: 80/20) | 15 | 15 | 15 | 15 | 15 |
| Hyaluronic acid | 0 | 0.5 | 0.5 | 0 | 0 |
| Carboxymethylcellulose | 0 | 0 | 0 | 5 | 5 |
| NaCl | 0 | 0 | 1 | 0 | 0.1 |

EXAMPLE 15-18

Preparation of Thermosensitive Composition for Mucoadhesive Measurement

The temperature-sensitive compositions were prepared using the same manner as in Examples 8-9 and 13-14, except that each concentration of carboxymethylcellulose component has been replaced with a concentration of 1% by weight of the final composition. The formulations of the prepared compositions are shown in the following Table 3.

TABLE 3

| | Content (w/v %) | | | |
|---|---|---|---|---|
| Component | Example 15 | Example 16 | Example 17 | Example 18 |
| Lysine-Pluronic F-127 | 15 | 15 | 0 | 0 |
| Lysine-and Cysteine-Pluronic F-127 (Lysine/Cysteine: 80/20) | 0 | 0 | 15 | 15 |
| Carboxymethylcellulose | 1 | 1 | 1 | 1 |
| NaCl | 0 | 0.1 | 0 | 0.1 |

EXPERIMENTAL EXAMPLE 1

Rheology Characterization (1) Preparation of Amino Acid-Modified Polymer Hydrogels Each of amino acid-modified Pluronic F-127 prepared from Examples 1-5 was dissolved in distilled water with a final concentration of 15% (w/v).

(2) Preparation of Polymer Compositions

Each hydrogel of the polymer compositions was prepared as described in Examples 6-14, and the formulations are shown in Tables 1 and 2.

(3) Preparation of Comparative Example 1

An amount of unmodified Pluronic F127, was added with a quantity of distilled water to form a polymer hydrogel with a final concentration of 15% (w/v).

(3) Measurement of Sol-Gel Phase Transition Temperature

The sol-gel phase transition temperature of the hydrogels prepared from Examples 1-5, hydrogel composites of Examples 6-14, and an unmodified counterpart of Comparative Example 1, were characterized using an HR10 rheometer (TA Instruments) equipped with a cone plate configuration and a metal cover that is to prevent solvent evaporation. The sol-gel phase transition temperature is defined as at a particular temperature in which the storage modulus and the loss modulus of a material are crossed with each other, which was measured in a range of 20° C. to 37° C. through oscillation mode with a temperature ramp of 2° C./min, a torque value of 100 µN.m, and a fixed frequency of 1 Hz. The measured results of the sol-gel phase transition temperature are presented in Table 4.

Table 4 demonstrates the sol-gel phase transition temperature of the hydrogels and hydrogel composites prepared from Examples 1-14. As shown in Table 4, firstly, it was confirmed all the prepared hydrogels and compositions having a property of temperature sensitivity. Secondly, the hydrogels prepared from Examples 1-6, and the composition of Example 10 all presented higher sol-gel phase transition temperature than that of Comparative Example 1. Significantly, the hydrogels prepared from Examples 2, 5(2), and 10 exhibited remarkably higher sol-gel phase transition temperature than that of Comparative Example 1, indicating more hydrogen bindings or interactions were formed between hydrogels and water, where the formation of hydrogen bindings or interactions should be attributed to the amino groups of Lysine or the thiol groups of cysteine in the polymer chains, so that the hydrophobic chains of these modified hydrogels may require higher temperature to aggregate, and eventually to form solid-like gels. Further, the compositions containing hyaluronic acid (HA) or carboxymethylcellulose (CMC) presented slight lower sol-gel phase transition temperature than that of their main components. This should be attributed to the water-absorption properties of the hyaluronic acid (HA) and carboxymethylcellulose (CMC). Generally, in a certain range, the sol-gel phase transition temperature of the Pluronic-based hydrogels decreases with increasing concentration of the Pluronic, so as the water of the composition has been partially absorbed by the added component of the carboxypolysaccharide, an amount of hydrogen bonds between carboxypolysaccharide and surrounding water is formed, so that the relative concentration of Pluronic in the composition is increased, resulting in decreasing the sol-gel phase transition temperature of the composition. Furthermore, the same mechanism can be used to explain why the compositions containing HA or CMC with NaCl presented lowest sol-gel phase transition temperature than those of that prepared without addition of NaCl. As the NaCl dissolved in the surrounding water, an amount of sodium ions may form strong interactions with surrounding water and the carboxypolysaccharide through an ionic binding, which may immobilize the water molecules and may increase the relative concentration of the Pluronic in the composition, resulting in a dramatic decrease of the sol-gel phase transition temperature of the composition. Through the measurement results of the sol-gel phase transition temperature, it is found that the addition of a carboxypolysaccharide with a metal ion may greatly influence the sol-gel phase transition temperature, and the metal ion may be useful to adjust the sol-gel phase transition temperature of a composition.

TABLE 4

| | Sol-gel phase transition temperature (° C.) |
|---|---|
| Example 1 (1) | 30 |
| Example 1 (4) | 29 |
| Example 2 | 33 |
| Example 3 (1) | 28 |
| Example 3 (2) | 28 |
| Example 4 | 28 |
| Example 5 (1) | 27 |
| Example 5 (2) | 33 |
| Example 6 | 30 |
| Example 7 | 29 |
| Example 8 | 31 |
| Example 9 | 24 |
| Example 10 | 33 |
| Example 11 | 30 |
| Example 12 | 27 |
| Example 13 | 30 |
| Example 14 | 25 |
| Comparative Example 1 | 26 |

EXPERIMENTAL EXAMPLE 2

Measurement of Polymer Residence Time In Vitro (1) Preparation of Amino Acid-Modified Polymer Hydrogels Each of amino acid-modified Pluronic F-127 prepared from Examples 1-5 was dissolved in distilled water with a final concentration of 15% (w/v).

(2) Preparation of Hydrogel Compositions

Each hydrogel of the polymer compositions was prepared as described in Examples 6-14, and the formulations are shown in Tables 1 and 2.

(3) Preparation of Comparative Example 1

An amount of Pluronic F127, was added with a quantity of distilled water to form a polymer hydrogel with a final concentration of 15% (w/v).

(4) Preparation of Comparative Example 2

An amount of hyaluronic acid, was added with a quantity of distilled water to form a polymer gel with a final concentration of 0.5% (w/v).

(5) Preparation of Comparative Example 3

An amount of carboxymethylcellulose, was added with a quantity of distilled water to form a polymer gel with a final concentration of 5% (w/v)

(5) Residence Time Measurement

In this invention, the methodology applied to measure the residence time of the prepared polymer hydrogels refers to the U.S. Pat. No. 10,105,387.

Briefly, 1 mL of each polymer hydrogels prepared from Examples 1-5 and in Comparative Examples 1, 2, and 3 were added to an individual vial of 7 mL. Then, all the vials were placed in an incubator at 37° C. to obtain solid polymer hydrogels. After all hydrogels in each individual vial were in gel phase, 1mL of phosphate buffer solution (PBS, pH 7.4) was added thereto. Afterwards, the phosphate buffer solution on the surface layer of the prepared polymer gel was removed in a fixed time interval once a day while storing the vial in an incubator at 37° C. The residual volume of the polymer gel was observed to measure an in-vitro polymer residence time, and the results are demonstrated in Table 5.

As shown in Table 5, the gel residence time of the hydrogels prepared from Examples 1 to 5 were all longer than that of Comparative Example 1, ranging from 4 to 18 days. Significantly, hydrogels prepared from Examples 2 and 5(2) showing remarkably superior gel residence time, 16 and 18 days, respectively. Comparative Example 1 was not modified with any type of amino acid, showing the shortest gel residence time, about 2 days. These results suggest that Pluronic hydrogel with amino acid modification increase the hydrogen bonds in the polymer chain, hydrogen bonds between the polymer chains, and hydrogen bonds between polymer chain and surrounding water, thereby, improving the ability of water-erosion resistance on the hydrogel. Moreover, Lysine- and Cysteine-modified Pluronic hydrogels provide additional concrete evidence for the improvement on the water-erosion resistance, because their amine and thiol groups tend to form hydrogen bonds or even form disulfide bonds (through thiol groups), which eventually lead to a great enhancement of the gel stability against water erosion. As a conclusion, the present invention provides an amino acid-modified Pluronic compound with an improved gel residence time as compared with the unmodified Pluronic.

Generally, the time for a wound to heal varies depending on the degree of the wound, but is about 7 days. Therefore, to prevent an occurrence of tissue adhesion during a wound healing process, a designed composition should have a formulation having a gel residence time longer than 7 days.

Herein, the present invention aims to provide a designed composition with a prolonged gel residence time much longer than 7 days, and it is assumed that a composition having a gel residence time more than 21 days may present efficient antiadhesion effects. As shown in Table 5, it is confirmed that the gel residence time of the hydrogel compositions of Examples 6 to 14 were all longer than that of Comparative Examples 1,2, and 3, and many of them exhibit a prolonged gel residence time over than 21 days. Further, by comparing the hydrogels from Example 2, with the hydrogel compositions of Examples 6 to 9, it is revealed that the addition of hyaluronic acid may slightly increase the mechanical strength of the composition (from 16 to 17 days), and the addition of hyaluronic acid with sodium chloride could greatly improve the gel residence time of the composition (from 17 to over than 21 days). Interestingly, the addition of carboxymethylcellulose could significantly increase the mechanical strength of the composition (from 16 to 21 days), and the addition of carboxymethylcellulose with sodium chloride could greatly extend the gel residence time of the composition (from 16 to over than 21 days). Further, by comparing the hydrogels prepared from Examples 2 and 5(2) with the hydrogel compositions of Examples 10 to 14, it is showed that the polymer combination (Example 10) prepared from mixing of 80% Example 2 with 20% Example 5(2) exhibiting rationally increased gel residence time between Examples 2 and 5(2). Significantly, when Example 10 was used as the main component of a hydrogel composition, the additions of hyaluronic acid or carboxymethylcellulose, with or without sodium chloride, all exhibited remarkably prolonged gel residence time, over than 21 days. These results suggest that the additions of carboxypolysacchride with and without metal ion to the amino acid-modified Pluronic F-127, should be able to increase the mechanical strength of the composition, and may promote formation of more interactions among each component in the composition, so as to reinforce and stabilize the hydro-structure of the composition, eventually resulting in extending the gel residence time of the hydrogel composition.

TABLE 5

|  | Gel residence time (day) |
| --- | --- |
| Example 1 (1) | 4 |
| Example 1 (4) | 4 |
| Example 2 | 16 |
| Example 3 (1) | 4 |
| Example 3 (2) | 4 |
| Example 4 | 4 |
| Example 5 (1) | 4 |
| Example 5 (2) | 18 |
| Example 6 | 17 |
| Example 7 | 21 |
| Example 8 | 21 |
| Example 9 | >21 |
| Example 10 | 17 |
| Example 11 | >21 |
| Example 12 | >21 |
| Example 13 | >21 |
| Example 14 | >21 |
| Comparative Example 1 | 2 |
| Comparative Example 2 | 2 |
| Comparative Example 3 | 3 |

EXPERIMENTAL EXAMPLE 3

In Vitro Mucoadhesive Measurement (1) Preparation of Polymer Compositions in Solutions.

Each solution of polymer composition was prepared as described in Table 6. To be noted, the carboxymethylcellulose with a final concentration of 1% (w/v) was used in Examples 15-18 due to encountering of a major measurement problem. When 5% (w/v) of carboxymethylcellulose was used as a component, the composition exhibited an extremely high viscosity, so that the mucoadhesive property of the composition cannot be precisely measured. Therefore, by decreasing the concentration of carboxymethylcellulose, the problem can be solved and the trend for the differences of mucoadhesive properties between different formulations can still be observed. The formulations of the measured compositions are shown in the following Table 6.

TABLE 6

| | Content (w/v %) | | | | | | | | |
| --- | --- | --- | --- | --- | --- | --- | --- | --- | --- |
| Component | Example 6 | Example 7 | Example 10 | Example 11 | Example 12 | Example 15 | Example 16 | Example 17 | Example 18 |
| Lysine-Pluronic F-127 | 15 | 15 | 0 | 0 | 0 | 15 | 15 | 0 | 0 |
| Lysine-and Cysteine-Pluronic F-127 (Lysine/Cysteine: 80/20) | 0 | 0 | 15 | 15 | 15 | 0 | 0 | 15 | 15 |
| Hyaluronic acid | 0.5 | 0.5 | 0 | 0.5 | 0.5 | 0 | 0 | 0 | 0 |
| Carboxymethylcellulose | 0 | 0 | 0 | 0 | 0 | 1 | 1 | 1 | 1 |
| NaCl | 0 | 1 | 0 | 0 | 1 | 0 | 0.1 | 0 | 0.1 |

(2) Preparation of Comparative Example 1

An amount of Pluronic F127, was added with a quantity of ultrapure water to form a polymer hydrogel with a final concentration of 15% (w/v).

(3) Preparation of Mucin Solution

The mucin solution was prepared by dissolving the mucin powder in ultrapure water to obtain a 5% (w/v) solution. In detail, an amount of mucin was added slowly to 100 ml ultrapure water under gentle magnetic stirring (200 rpm), in a cold water-bath maintained at 4° C. At the end of the preparation, the mucin solution was stored at 4° C. until use.

(4) Preparation of Polymer Composition-Mucin Mixtures

Each of the polymer compositions prepared in solutions as shown in Table 5, and the unmodified polymer powder prepared in Comparative Example 1 as described in (2), were individually mixed with the prepared 5% (w/v) of mucin solution to obtain a 15% (w/v) polymer composition-mucin mixture.

(5) In Vitro Mucoadhesive Determination

A rheological method was used to obtain a predictive and indirect evaluation of hydrogel mucoadhesion (Hassan, E. E., et al., *A Simple Rheological Method for the in Vitro Assessment of Mucin-Polymer Bioadhesive Bond Strength*, Pharm Res 7, 491-495, 1990). The mucoadhesive properties of the composition solutions prepared from Examples 6-7, 10-12, and 15-18, the unmodified counterpart of Comparative Example 1, the prepared mucin solution, and the mixtures of the polymer composition and mucin solutions, were evaluated using an HR10 rheometer (TA Instruments) equipped with a cone plate configuration and a protective metal cover that is to prevent solvent evaporation. The rheological analysis was performed using flow mode in a shear rate of 10 s$^{-1}$ at 37° C., and each analysis was preceded by a resting time of 5 min at room temperature in order to avoid structural alteration caused by thermal shock.

This experiment is based on the evaluation of the measured viscosity of a dispersion obtained from the mixture of the polymer composition and a solution of mucin. The degree of interaction between the composition and mucin is the measurement of the final viscosity of the mixture ($\eta_{final}$), which represents a parameter to an established interaction between these components, and can be calculated by the following equation:

$$\eta_{final} = \eta_{mixture} - (\eta_{polymer\ composition} + \eta_{miucin})$$

where:

$\eta_{mixture}$=viscosity of the mixture comprising polymer composition and mucin $\eta_{polymer\ composition}$=viscosity of the polymer composition $\eta_{mucin}$=viscosity of mucin In the case of interactions between the polymer and mucin, the value of $\eta_{final}$>0 (Mayol L., et al., *A novel poloxamers/hyaluronic acid in situ forming hydrogel for drug delivery: Rheological, mucoadhesive and in vitro release properties*, Eur J Pharm Biopharm 70(1); 199-206, 2008), and the results are displayed in Table 7.

As shown in Table 7, the mucoadhesive properties of the polymer compositions prepared in all Examples were represented with the calculated viscosity of $\eta_{final}$. Clearly, the polymer compositions of Examples 10 and 15-18 exhibited a certain degree of mucoadhesive properties, and they were all with significant higher values than that of Comparative Example 1. while the polymer composition from other Examples all exhibiting negative values of $\eta_{final}$, suggesting that the use of carboxymethylcellulose as a component should result in an increase of the mucoadhesive properties to the polymer compositions while the use of hyaluronic acid would gain the opposite results. In addition, Examples 16 and 18 showed remarkably higher values of $\eta_{final}$ as compared with Example 17, indicating the addition of metal ion would promote the mucoadhesive property of the composition. These results can be attributed to the natural property of the carboxymethylcellulose. The carboxymethylcellulose has been reported to possess excellent tissue adhesiveness due to its multiple carboxyl groups which are able to form hydrogen bonds with tissues. Moreover, the addition of metal ion may further introduce more interactions among carboxymethylcellulose, polymer, and tissues, resulting boosted effects on increasing of mucoadhesive properties of the compositions.

In addition, the polymer composition of Example 10 itself without adding carboxymethylcellulose exhibited significant strong mucoadhesive properties, which can be explained as the polymer composition possesses available side-chains where an amine group from Lysine and a thiol group from cysteine are able to form hydrogen bonds and/or disulfide bonds with mucin. As a result, this polymer composition are able to present strong mucoadhesive properties.

TABLE 7

|  | $\eta_{mixture}$ | $\eta_{polymer}$ | $\eta_{mucin}$ | $\eta_{final}$ |
| --- | --- | --- | --- | --- |
| Comparative Example 1 | 13.80 | 10.16 | 0.04 | 3.60 |
| Example 6 | 35.17 | 44.08 | 0.04 | <0 |
| Example 7 | 65.35 | 72.11 | 0.04 | <0 |
| Example 10 | 110.81 | 26.98 | 0.04 | 83.79 |
| Example 11 | 68.57 | 98.37 | 0.04 | <0 |
| Example 12 | 77.32 | 95.73 | 0.04 | <0 |

TABLE 7-continued

|  | $\eta_{mixture}$ | $\eta_{polymer}$ | $\eta_{mucin}$ | $\eta_{final}$ |
| --- | --- | --- | --- | --- |
| Example 15 | 69.60 | 56.16 | 0.04 | 13.40 |
| Example 16 | 144.39 | 31.91 | 0.04 | 112.43 |
| Example 17 | 130.03 | 73.66 | 0.04 | 56.32 |
| Example 18 | 174.77 | 73.77 | 0.04 | 100.96 |

EXPERIMENTAL EXAMPLE 4

Test of Adhesion Prevention Efficacy in Animal Model (1) Preparation of Comparative Example 1

An amount of Pluronic F127, was added with a quantity of distilled water to form a polymer hydrogel with a final concentration of 15% (w/v).

(2) Preparation of Hydrogel Compositions

Each hydrogel of the polymer compositions was prepared as described in Examples 6-14, and the formulations are shown in Tables 1 and 2.

(2) Animal Test

A rat model of sidewall defect-cecum abrasion with some modification was performed to evaluate the tissue-adhesion prevention efficacy of the provided polymer compositions. Herein, polymer compositions prepared in Examples 6-14 were used as the experimental groups, an unmodified counterpart prepared in Comparative Example 1 was used as a comparative group, and a control group was used in which no material was applied to the surgical site.

In the animal test, 4 of male Sprague Dawley (SD) rats per group were intraperitoneally anesthetized by injecting 1 mL/Kg of mixture containing Zoletil® and Rompun® (1:1). The anesthetized rats were shaved and disinfected with povidone, and the peritoneum was opened by a 5 cm-long incision along the linea alba on the abdominal wall. Then, a 1×2 cm$^2$ peritoneal defect on the right abdominal wall was created using scalpel.

The cecum defect was created using sterile surgical gauze to abrade the serosa until it was damaged and hemorrhaging but not perforated. Afterwards, the damaged cecum and the injured abdominal wall were sutured using 3-0 silk sutures in order to force adhesions to occur. For the experimental groups, 0.5 mL of each hydrogels prepared in Examples 6-14 and in Comparative Example 1, were individually and uniformly applied to the injured sites, and gelation occurred in situ within 2 min. For the control group, the defects were washed with 0.5 mL of sterile normal saline. Finally, the peritoneum was closed with interrupted 3-0 silk suture, and the skin was closed with 4-0 silk sutures, respectively.

At 10 days after surgery, the degree of tissue adhesions was examined in a double-blind manner according to the Hoffmann adhesion scoring system in which the higher in score, the more severe in tissue adhesion.

The detailed description for examination the degree of tissue adhesion using the Hoffmann adhesion scoring system is provided in the following Table 8 (Hoffmann N E., et al., *Choice of hemostatic agent influences adhesion formation in a rat cecal adhesion model*, J Surg Res.155(1), 77-81, 2009). The evaluated quantitative results of the tissue adhesion degree are presented in Table 9 and can be graphically illustrated in FIG. 1, where the statistical analysis was performed by one-way analysis of variance (ANOVA) with two-tailed calculation using Prism 9 for Mac (GraphPad Software, USA), and the differences between the control and experiment groups were considered statistically significant if p<0.05. The photographic illustrations of the tissue adhesions for control, comparative groups and experimental groups are displayed in FIGS. 2(A-K).

As shown in Table 9 (Also see FIG. 1), the hydrogels prepared in Examples 6-14 all showed a significant inhibition of tissue adhesion, while the hydrogel prepared in Comparative Example 1 exhibited insignificant effects on preventing tissue adhesion as compared with the control group (Also see FIGS. 2(A-K)). In particular, the hydrogels prepared from Examples 9, 13 and 14 exhibited remarkably excellent efficacy in preventing tissue adhesion. Further, as shown by the gel residence results, Examples 9, 13 and 14 all exhibited a prolonged gel residence time over than 21 days. These results suggested hydrogels having longer residence time should be more effective to prevent tissue adhesion, which also supported our assumption. However, Examples 7 and 11-12 also exhibited a longer gel residence time over than 21 days, but did not present superior antiadhesive properties (See FIGS. 2(D, H-J)). This can be attributed to their mucoadhesive properties. The mucoadhesiveness of an adhesion preventer could be crucial if an adhesion inhibitor cannot firmly adhere to the wound tissues, it may undergo a deformation during some necessary activities, which could reduce the coverage, leading to insufficient prevention of tissue adhesions. As shown by the results of the mucoadhesion measurements, compositions of Examples 7 and 11-12 all presented negative values of $\eta_{final}$, indicating a poor interaction between these compositions and mucin, which may further influence their antiadhesive abilities.

In conclusion, to design an ideal adhesion inhibitor, the residence time is not the only one aspect of consideration, the mucoadhesive properties should also be carefully taken into account. The present invention provides one or some designed polymer compositions that are not only presenting prolonged residence time, but also exhibiting significant mucoadhesive properties, which make the polymer compositions an excellent adhesion preventer.

TABLE 8

| Score | Description |
| --- | --- |
| Area Score | |
| 0 | No adhesion |
| 1 | Cecum to bowel adhesion |
| 2 | Cecum to sidewall adhesion over less than 25% of the abrade surface area |
| 3 | Cecum to sidewall adhesion between 25% and 50% of the abrade surface area |
| 4 | Cecum to sidewall adhesion over more than 50% of the abrade surface area |
| Strength Score | |
| 0 | No adhesion |
| 1 | Gentle traction required to break adhesion |
| 2 | Blunt dissection required to break adhesion |
| 3 | Sharp dissection required to break adhesion |
| Extend Score | |
| 0 | No adhesion |
| 1 | Filmy avascular adhesion |
| 2 | Vascular adhesion |
| 3 | Opaque or Cohesive adhesion |

TABLE 9

| | Hoffmann Score$^a_{Total}$ | Statistically Significant Difference (Comparing with Control Group) |
| --- | --- | --- |
| Control Group | 8.50 ± 0.50 | |
| Comparative Example 1 | 4.00 ± 1.41 | ns |
| Example 6 | 2.75 ± 1.60 | ** |
| Example 7 | 1.00 ± 1.00 | *** |
| Example 8 | 1.75 ± 1.75 | ** |
| Example 9 | 0.00 ± 0.00 | **** |
| Example 10 | 1.50 ± 1.50 | ** |
| Example 11 | 1.50 ± 0.87 | ** |
| Example 12 | 2.75 ± 1.60 | ** |
| Example 13 | 0.00 ± 0.00 | **** |
| Example 14 | 0.00 ± 0.00 | **** |

$^a$Mean ± SEM (n = 4);
* p < 0.05;
** p < 0.01;
*** p < 0.001;
**** p < 0.0001;
ns: not significant difference

EXPERIMENTAL EXAMPLE 5

Loading, Encapsulation, and Release of Pharmaceutically Active Agent (1) Preparation of solution mixture of PTX and amino acid-modified polymer combination 12 mg of PTX were first dissolved in 8 mL of methanol. Afterwards, 1 g of polymer from Example 10 containing 800 mg and 200 mg of Lysine-modified and Cysteine modified Pluronic F-127, respectively, was dissolved in the PTX-methanol solution to obtain a mixture of PTX-amino acid-modified polymer combination.

(2) Preparation of Comparative Example 1

12 mg of PTX were dissolved in 8 mL of methanol. 1 g of unmodified Pluronic F-127 was added to a PTX-methanol solution to form a PTX-Pluronic F-127 mixture.

(3) Drug Loading and Encapsulation

Herein, Paclitaxel is selected as a pharmaceutically active agent, which is loaded and encapsulated using thin-film hydration method (Wei Z., et al., *Paclitaxel-Loaded Pluronic P123/F127 Mixed Polymeric Micelles: Formulation, Optimization and In Vitro Characterization*, Int. J. Pharm, 376 (1), 176-185, 2009). Briefly, the mixtures of drug and amino acid-modified polymer prepared in Comparative Example 1 and Example 10, were respective transferred into an individual eggplant-shaped glass bottle and proceeded with rotatory evaporation for 1 hour to remove methanol. When methanol was removed, a layer of PTX-loaded polymer thin film was formed in the bottle, which was then placed in a vacuum oven at 50° C. overnight for a completed solvent removal. Each of the PTX-loaded polymer thin films was rehydrated with 8 mL of distilled water to encapsulate the PTX followed by filtration using 23 μm cellulose membrane to remove the unencapsulated PTX. Afterwards, each of the PTX-encapsulated polymers was proceeded with lyophilization to yield PTX-polymer powders for evaluation of the drug-loading capacity and drug encapsulation efficacy.

The equations for calculation of drug-loading capacity and drug encapsulation efficacy were provided as following, $$\text{Drug loading capacity} = \frac{\text{weight of the drug in micelles}}{\text{weight of the feeding polymer and drug}} \times 100\%$$

$$\text{Drug encapsulation efficacy} = \frac{\text{weight of the drug in micelles}}{\text{weight of the feeding drug}} \times 100\%$$

and the results are displayed in Table 10.

TABLE 10

|  | PTX-loading (%) | PTX encapsulation (%) |
|---|---|---|
| Example 10 | 1.18 | 90.2 |
| Comparative Example 1 | 1.09 | 88.2 |

As shown in Table 9, it was confirmed that hydrogel prepared in Example 10 showed an improved drug-loading capacity and PTX encapsulation efficacy as compared with Comparative Example 1.

(4) Drug Release

Herein, the drug release profile is examined using membrane-less diffusion method (Zhang L., et al., *Development and In-Vitro Evaluation of Sustained Release Poloxamer 407 (P407) Gel Formulations of Ceftiofur*, J. Controlled Release, 85 (1), 73-81, 2002). Briefly, 50 mg of carboxymethylcellulose was firstly added to the PTX-encapsulated polymer powders prepared from Example 10 to obtain a composition, in which the final polymer components were same as Example 13. Then, the sample of the PTX-encapsulated polymer powders prepared from Comparative Example 1, and the sample of the obtained composition, were respective placed in a corresponding beaker, and rehydrated to form a PTX-polymer hydrogel containing 20% (w/v) of polymer or polymer composition; herein, the PTX-unmodified Pluronic hydrogel with a polymer content of 20% (w/v) was prepared from Comparative Example 1 and served as a comparative sample. Then, each beaker containing the prepared PTX-polymer hydrogel, was prewarmed in an incubator at 37° C. to retain a gel state. Afterwards, 25 mL of prewarmed release medium containing PBS-methanol mixed solution (90%:10%; v/v) were directly added onto the surface of each prepared PTX-polymer hydrogel, which was then placed in an incubator at 37° C. with a shaking speed of 100 rpm. At predetermined time, 1 mL of solution was taken from each beaker for examination of drug release, and 1 mL of release medium was subsequently added to remain the sink condition. The drug release tests on the prepared composition and on Comparative Example 1 were performed in triplicate and the drug-release data were detected by UV-Vis spectrometer in which the UV wavelength was set at 236 nm. The analyzed drug release profiles are displayed in FIGS. 3(A-B).

Figure 3A:
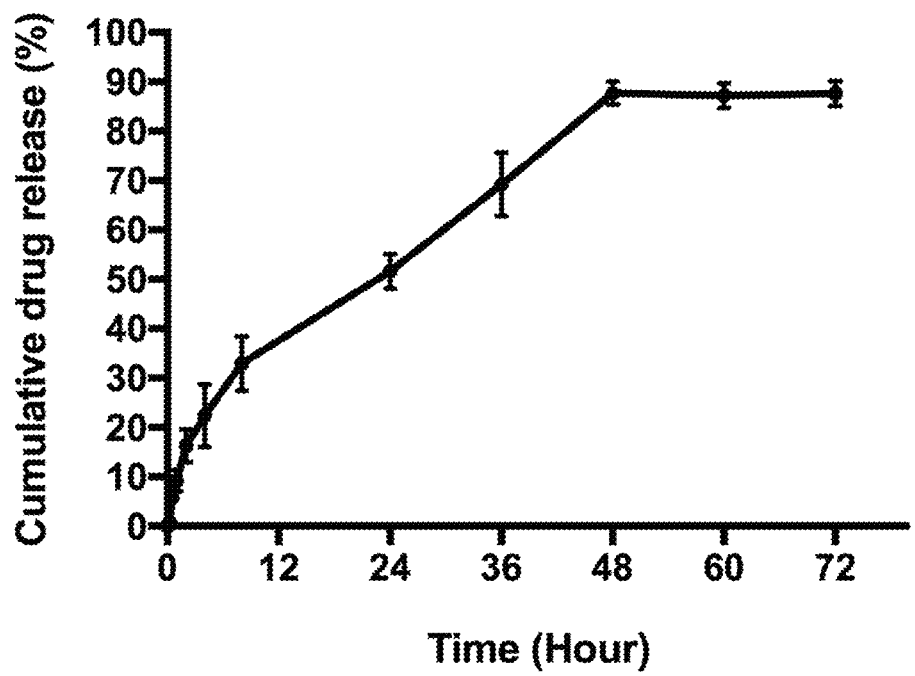
FIG. 3A illustrates the PTX release profile of the hydrogel prepared from Comparative Example 1.
Figure 3B:
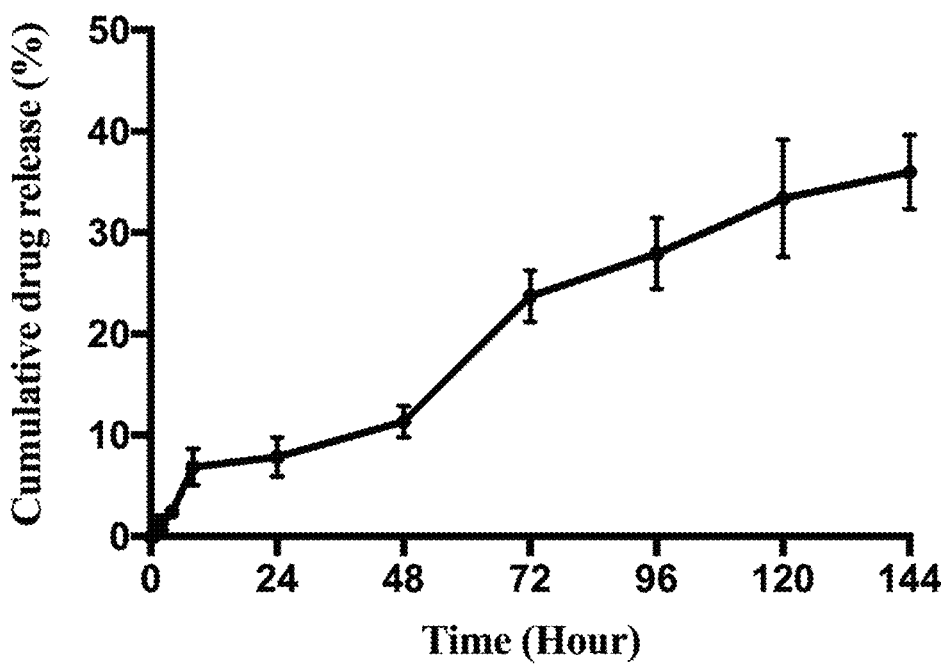
FIG. 3B illustrates the PTX release profile of the hydrogel composition prepared from Example 10, where the polymer combination was first loaded with PTX, and an amount of carboxymethylcellulose was subsequently added to the formed PTX-polymer combination to obtained a PTX-polymer-5%(w/v) CMC composition.

FIG. 3A demonstrates the PTX release profile of the hydrogel prepared from unmodified Pluronic F-127. As shown in FIG. 3A, about 50% of the encapsulated PTX was released within 24 hours, and all PTX was completely released from the unmodified Pluronic F-127 within 48 hours, showing a rapid drug release behavior. In addition, about 30% of the encapsulated PTX was released within the first 12 hours, indicating that a dumping drug release occurred. FIG. 3B demonstrate the PTX release pattern of the hydrogel that contained the same components with Example 13, where the PTX was first encapsulated by composition of Example 10, and an amount of carboxymethylcellulose was subsequently added to the obtained PTX-polymer. As shown in FIG. 3B, in the first 24 hours, less than 10% of PTX was released from the hydrogel prepared from Example 10, and less than 40% of PTX was slowly released in the following 144 hours, showing a remarkably sustainable drug release profile of this hydrogel composition. These results could be attributed to the differences of the mechanical strengths between these two hydrogels. As shown by the gel residence results of Example 13 in Experimental Example 2, the hydrogel composition of Example 13 exhibited extremely prolonged gel residence time in comparison to the hydrogel prepared in Comparative Example 1.

To conclude, on the basis of our experimental results, it is confirmed that a Pluronic-based drug release system can be greatly improved on its drug loading capability and drug encapsulation efficacy by using a polymer combination consisting of different amino acid-modified Pluronic polymers. Furthermore, the drug-release sustainability can be greatly enhanced by using composition comprising a combination of different amino acid-modified Pluronic polymers with a carboxypolysaccharide.

In summary, the present inventions have found that a composition comprising an amino acid-modified Pluronic/ combination and a carboxypolysaccharide with or without a metal ion may: (1) enhance the mechanical strength of the polymer structure, (2) increase the water-erosion resistance ability, (3) increase the adhesiveness between the polymer and tissues, (4) enhance the tissue adhesion prevention ability, and (5) improve the release profile in delivery of pharmaceutically active agents.

While the invention has been described in detail with reference to the aforesaid preferred embodiments, it should be appreciated that the foregoing description should not be construed as limiting the invention. Various modifications and substitutions will be apparent to those skilled in the art upon reading the foregoing contents. Accordingly, the scope of the invention should be defined by the appended claims.

What is claimed is:

1. A composition comprising a polymer, and a carboxypolysaccharide, wherein the polymer having any one structure of the following formula (I):

or a combination thereof,
wherein:
POLY is a triblock copolymer of poly(ethylene oxide)-poly(propylene oxide)-poly(ethylene oxide);
m and n are independently from each other 0 or 1, wherein m and n cannot be 0 simultaneously; and
AA is an amino acid residue, where its amino group directly binds to the chain-end of the POLY to form carbamate (O—C(=O)—NH) linkage.

2. The composition of claim 1, wherein the carboxypolysaccharide is one or more selected from the group consisting of carboxymethylcellulose (CMC), carboxyethylcellulose, hyaluronic acid (HA), alginate, carboxymethyl chitosan, pectin, carboxymethyl dextran, heparin sulfate, and chondroitin sulfate.

3. The composition of claim 1, wherein POLY has an average molecular weight ranging from 1,000 to 20,000 Daltons.

4. The composition of claim 1, wherein any one of the polymer or the combination thereof is in an amount of 5% to 30% by weight of the composition.

5. The composition of claim 1, wherein the carboxypolysaccharide has a molecular weight in a range of 50 kg/mol to 4,000 kg/mol.

6. The composition of claim 1, wherein the content of the carboxypolysaccharide is in an amount of 0.1% to 20% by weight of the final composition.

7. The composition of claim 1, wherein POLY is selected from the group consisting of Poloxamer 407, Poloxamer 188 and Poloxamer 105.

8. The composition of claim 1, wherein the amino acid residue is selected from the groups consisting of hydrophobic amino acids, hydrophilic amino acids, basic amino acids, acidic amino acids, and aromatic amino acids.

9. The composition of claim 1, wherein POLY is a Poloxamer, and AA is selected from the group consisting of Leucine, Methionine, Lysine, Aspartic acid, Asparagine, Tyrosine, Serine, and Cysteine.

10. The composition of claim 1, wherein the combination is two or more of formula (I) mixed, wherein POLY is a Poloxamer 407, and AA is selected from the group consisting of Lysine, Serine, and Cysteine.

11. The composition of claim 1, furthering comprising a metal ion.

12. The composition of claim 11, wherein the metal ion is one or more selected from the group consisting of $Na^+$, $^+$, $Ag^+$, $Cu^{+2}$, $Mg^{+2}$, $Ca^{+2}$, $Zn^{+2}$, $Al^{+3}$, $Fe^{+3}$, $Se^{+4}$, and $Ti^{+4}$.

13. The composition of claim 1, further comprising a pharmaceutically active agent.

14. The composition of claim 13, wherein the pharmaceutically active agent is selected from the group consisting of anticancer drugs, antibiotics, hemostatic agents, steroids, non-steroidal anti-inflammatory drugs, hormones, analgesics, and anesthetics.

15. A method of preventing postoperative tissue adhesion, comprising administering a composition of claim 1, wherein the composition has powder, solution, or gel form, and is applied by coating or spraying onto a wound site and the surfaces of surrounding tissues.

16. A method of drug delivery, comprising administering a composition of claim 1, wherein the composition has powder, solution, or gel form, and is applied by coating or spraying onto a wound site and the surfaces of surrounding tissues.

* * * * *